(12) United States Patent
Doxey et al.

(10) Patent No.: US 10,925,689 B2
(45) Date of Patent: Feb. 23, 2021

(54) NITRIC OXIDE RELEASING NAIL COATING COMPOSITIONS, NITRIC OXIDE RELEASING NAIL COATINGS, AND METHODS OF USING THE SAME

(71) Applicant: Novan, Inc., Morrisville, NC (US)

(72) Inventors: Ryan Doxey, Raleigh, NC (US); Yong Zhang, Cary, NC (US)

(73) Assignee: Novan, Inc., Morrisville, NC (US)

( * ) Notice: Subject to any disclaimer, the term of this patent is extended or adjusted under 35 U.S.C. 154(b) by 223 days.

(21) Appl. No.: 15/324,526

(22) PCT Filed: Jul. 14, 2015

(86) PCT No.: PCT/US2015/040319
§ 371 (c)(1),
(2) Date: Jan. 6, 2017

(87) PCT Pub. No.: WO2016/010988
PCT Pub. Date: Jan. 21, 2016

(65) Prior Publication Data
US 2017/0196905 A1   Jul. 13, 2017

Related U.S. Application Data

(60) Provisional application No. 62/024,200, filed on Jul. 14, 2014.

(51) Int. Cl.
| | | |
|---|---|---|
| *A61C 3/02* | (2006.01) | |
| *A61K 31/695* | (2006.01) | |
| *A61K 47/10* | (2017.01) | |
| *A61K 9/06* | (2006.01) | |
| *A61K 9/70* | (2006.01) | |
| *A61K 8/25* | (2006.01) | |
| *A61K 8/19* | (2006.01) | |
| *A61K 9/00* | (2006.01) | |
| *A61K 8/73* | (2006.01) | |
| *A61K 8/81* | (2006.01) | |
| *A61K 33/00* | (2006.01) | |
| *A61K 47/32* | (2006.01) | |
| *A61K 47/38* | (2006.01) | |
| *A61P 31/10* | (2006.01) | |

(52) U.S. Cl.
CPC .................. *A61C 3/02* (2013.01); *A61K 8/19* (2013.01); *A61K 8/25* (2013.01); *A61K 8/731* (2013.01); *A61K 8/8182* (2013.01); *A61K 9/0014* (2013.01); *A61K 9/06* (2013.01); *A61K 9/7015* (2013.01); *A61K 31/695* (2013.01); *A61K 33/00* (2013.01); *A61K 47/10* (2013.01); *A61K 47/32* (2013.01); *A61K 47/38* (2013.01); *A61P 31/10* (2018.01); *A61K 2800/22* (2013.01); *A61K 2800/88* (2013.01); *A61K 2800/884* (2013.01)

(58) Field of Classification Search
CPC .......... A61Q 3/02; A61K 47/32; A61K 8/731; A61K 8/8182; A61K 33/00; A61K 47/38; A61K 8/19; A61K 8/25; A61K 9/0014; A61K 9/06; A61K 31/695; A61K 2800/884; A61K 2800/88; A61K 9/7015
See application file for complete search history.

(56) References Cited

U.S. PATENT DOCUMENTS

| | | |
|---|---|---|
| 5,968,001 A | 10/1999 | Freeman |
| 6,709,681 B2 | 3/2004 | Benjamin et al. |
| 7,704,518 B2 | 4/2010 | Tamarkin et al. |
| 8,114,442 B2 | 2/2012 | Tucker et al. |
| 8,128,964 B2 | 3/2012 | Tucker et al. |
| 8,241,650 B2 | 8/2012 | Peters |
| 8,343,945 B2 | 1/2013 | Tamarkin et al. |
| 8,362,091 B2 | 1/2013 | Tamarkin et al. |
| 8,399,005 B2 | 3/2013 | Schoenfisch et al. |
| 8,486,374 B2 | 7/2013 | Tamarkin et al. |
| 8,591,876 B2 | 11/2013 | Bauman et al. |
| 8,617,100 B2 | 12/2013 | Eini et al. |
| 8,636,982 B2 | 1/2014 | Tamarkin et al. |
| 8,795,635 B2 | 8/2014 | Tamarkin et al. |
| 8,795,693 B2 | 8/2014 | Tamarkin et al. |
| 8,900,553 B2 | 12/2014 | Tamarkin et al. |
| 9,101,662 B2 | 8/2015 | Tamarkin et al. |
| 9,161,916 B2 | 10/2015 | Tamarkin et al. |
| 9,187,501 B2 | 11/2015 | Schoenfisch et al. |

(Continued)

FOREIGN PATENT DOCUMENTS

| | | |
|---|---|---|
| CA | 2 594 407 A1 | 8/2006 |
| EP | 1 707 224 A1 | 10/2006 |

(Continued)

OTHER PUBLICATIONS

Axelgaard "AmGel Hydrogels" *Product Information*—http://www.alexgaard.com/Products/Hydrogels (3 pages) (2017).
Chow et al. "Formulation of Hydrophilic Non-Aqueous Gel: Drug Stability in Different Solvents and Rheological Behavior of Gel Matrices" *Pharmaceutical Research* 25(1):207-217 (2007).
Covidien "Hydrogels: The Industry's Choice in Gel" *Product Brochure* (4 pages) (2009).
Finnen et al. "Topical application of acidified nitrite to the nail renders it antifungal and causes nitrosation of cysteine groups in the nail plate" *British Journal of Dermatology* 157:494-500 (2007).
McHale et al. "In Vitro and In Vivo Nail Penetration of Nitric Oxide Releasing Formulations for the Topical Treatment of Onychomycosis" *Abstract*—www.novantherapeutics.com (1 page) (2016).

(Continued)

*Primary Examiner* — Kyle A Purdy
(74) *Attorney, Agent, or Firm* — Myers Bigel, P. A.

(57) ABSTRACT

The present invention relates to nitric oxide (NO)-releasing nail coating compositions, NO-releasing coatings, and methods of using the same, for example, to treat fungal infections of a nail. It is noted that aspects described with respect to one embodiment may be incorporated in different embodiments although not specifically described relative thereto. Provided according to embodiments of the invention are nitric oxide (NO)-releasing nail coating compositions and/or coatings.

20 Claims, No Drawings

(56) References Cited

U.S. PATENT DOCUMENTS

| | | |
|---|---|---|
| 9,265,725 B2 | 2/2016 | Tamarkin et al. |
| 9,320,705 B2 | 4/2016 | Tamarkin et al. |
| 9,381,381 B2 | 7/2016 | Benjamin |
| 9,427,605 B2 | 8/2016 | Peters |
| 2004/0037897 A1 | 2/2004 | Benjamin et al. |
| 2004/0105898 A1 | 6/2004 | Benjamin et al. |
| 2005/0037093 A1 | 2/2005 | Benjamin |
| 2005/0038473 A1 | 2/2005 | Tamarkin et al. |
| 2005/0232869 A1 | 10/2005 | Tamarkin et al. |
| 2005/0271596 A1 | 12/2005 | Friedman et al. |
| 2006/0269620 A1 | 11/2006 | Morris et al. |
| 2006/0275218 A1 | 12/2006 | Tamarkin et al. |
| 2007/0292359 A1 | 12/2007 | Friedman et al. |
| 2007/0292461 A1 | 12/2007 | Tamarkin et al. |
| 2008/0031907 A1 | 2/2008 | Tamarkin et al. |
| 2008/0044444 A1 | 2/2008 | Tamarkin et al. |
| 2008/0063607 A1 | 3/2008 | Tamarkin et al. |
| 2008/0069779 A1 | 3/2008 | Tamarkin et al. |
| 2008/0138296 A1 | 6/2008 | Tamarkin et al. |
| 2008/0152596 A1 | 6/2008 | Friedman et al. |
| 2008/0166303 A1 | 7/2008 | Tamarkin et al. |
| 2008/0206155 A1 | 8/2008 | Tamarkin et al. |
| 2008/0206159 A1 | 8/2008 | Tamarkin et al. |
| 2008/0206161 A1 | 8/2008 | Tamarkin et al. |
| 2008/0253973 A1 | 10/2008 | Tamarkin et al. |
| 2008/0260655 A1 | 10/2008 | Tamarkin et al. |
| 2008/0292560 A1 | 11/2008 | Tamarkin et al. |
| 2008/0299220 A1 | 12/2008 | Tamarkin et al. |
| 2008/0317679 A1 | 12/2008 | Tamarkin et al. |
| 2009/0041680 A1 | 2/2009 | Tamarkin et al. |
| 2009/0068118 A1 | 3/2009 | Eini et al. |
| 2009/0130029 A1 | 5/2009 | Tamarkin et al. |
| 2009/0175799 A1 | 7/2009 | Tamarkin et al. |
| 2009/0214618 A1 | 8/2009 | Schoenfisch et al. |
| 2010/0015253 A1 | 1/2010 | Benjamin |
| 2010/0098733 A1 | 4/2010 | Stasko |
| 2010/0129474 A1 | 5/2010 | Benjamin et al. |
| 2010/0152683 A1 | 6/2010 | Lindgren et al. |
| 2010/0221195 A1 | 9/2010 | Tamarkin et al. |
| 2010/0239512 A1 | 9/2010 | Morris et al. |
| 2010/0266510 A1 | 10/2010 | Tamarkin et al. |
| 2010/0310476 A1 | 12/2010 | Tamarkin et al. |
| 2010/0331968 A1 | 12/2010 | Morris et al. |
| 2011/0045037 A1 | 2/2011 | Tamarkin et al. |
| 2011/0052650 A1 | 3/2011 | Morris et al. |
| 2011/0086234 A1 | 4/2011 | Stasko et al. |
| 2011/0097279 A1 | 4/2011 | Tamarkin et al. |
| 2011/0212033 A1 | 9/2011 | Tamarkin et al. |
| 2012/0134951 A1 | 5/2012 | Stasko et al. |
| 2012/0141384 A1 | 6/2012 | Tamarkin et al. |
| 2012/0237453 A1 | 9/2012 | Tamarkin et al. |
| 2012/0295952 A1 | 11/2012 | Collard et al. |
| 2013/0164225 A1 | 6/2013 | Tamarkin et al. |
| 2013/0189191 A1 | 7/2013 | Tamarkin et al. |
| 2013/0189193 A1 | 7/2013 | Tamarkin et al. |
| 2013/0189195 A1 | 7/2013 | Tamarkin et al. |
| 2014/0004176 A1 | 1/2014 | Fossel et al. |
| 2014/0105986 A1 | 4/2014 | Doxey et al. |
| 2014/0134321 A1 | 5/2014 | Stasko et al. |
| 2014/0171395 A1 | 6/2014 | Schoenfisch et al. |
| 2014/0193502 A1 | 7/2014 | Tamarkin et al. |
| 2014/0221331 A1 | 8/2014 | Barraud et al. |
| 2014/0248219 A1 | 9/2014 | Tamarkin et al. |
| 2014/0255318 A1 | 9/2014 | Stasko et al. |
| 2014/0271494 A1 | 9/2014 | Tamarkin et al. |
| 2015/0010656 A1 | 1/2015 | Perricone |
| 2015/0017103 A1 | 1/2015 | Tamarkin et al. |
| 2015/0025060 A1 | 1/2015 | Tamarkin et al. |
| 2015/0111973 A1 | 4/2015 | Bauman et al. |
| 2015/0118164 A1 | 4/2015 | Tamarkin et al. |
| 2015/0157729 A1* | 6/2015 | Petersson ............ A61K 9/0014 424/45 |
| 2015/0225488 A1 | 8/2015 | Schoenfisch et al. |
| 2016/0008275 A1 | 1/2016 | Doxey et al. |
| 2016/0199295 A1 | 7/2016 | Doxey et al. |
| 2016/0256484 A1 | 9/2016 | Doxey et al. |
| 2018/0200541 A1 | 7/2018 | Doxey et al. |

FOREIGN PATENT DOCUMENTS

| | | |
|---|---|---|
| EP | 1 861 130 B1 | 9/2008 |
| EP | 1 871 433 B1 | 4/2009 |
| EP | 1 846 058 B1 | 7/2009 |
| EP | 2 119 459 A1 | 11/2009 |
| EP | 2 142 179 A1 | 1/2010 |
| EP | 2 142 181 A1 | 1/2010 |
| EP | 1 917 005 B1 | 9/2010 |
| WO | WO 2005/004984 A1 | 1/2005 |
| WO | WO 2006/084910 A2 | 8/2006 |
| WO | WO 2006/084912 A1 | 8/2006 |
| WO | WO 2006/100154 A1 | 9/2006 |
| WO | WO 2007/007208 A2 | 1/2007 |
| WO | WO 2007/023005 A1 | 3/2007 |
| WO | WO 2007/023396 A2 | 3/2007 |
| WO | WO 2007/054818 A2 | 5/2007 |
| WO | WO 2008/032212 A2 | 3/2008 |
| WO | WO 2008/038140 A2 | 4/2008 |
| WO | WO 2008/038147 A2 | 4/2008 |
| WO | WO 2008/110872 A2 | 9/2008 |
| WO | WO 2008/116497 A1 | 10/2008 |
| WO | WO 2008/116925 A1 | 10/2008 |
| WO | WO 2008/152444 A2 | 12/2008 |
| WO | WO 2009/007785 A2 | 1/2009 |
| WO | WO 2009/049208 A1 | 4/2009 |
| WO | WO 2009/056991 A2 | 5/2009 |
| WO | WO 2009/072007 A2 | 6/2009 |
| WO | WO 2009/087578 A2 | 7/2009 |
| WO | WO 2009/090495 A2 | 7/2009 |
| WO | WO 2009/098595 A2 | 8/2009 |
| WO | WO 2010/044875 A2 | 4/2010 |
| WO | WO 2011/022652 A1 | 2/2011 |
| WO | WO 2011/022680 A2 | 2/2011 |
| WO | WO 2011/047013 A1 | 4/2011 |
| WO | 2012078649 | 6/2012 |
| WO | WO 2012/082976 A1 | 6/2012 |
| WO | WO 2012/100174 A1 | 7/2012 |
| WO | WO 2012/118819 A2 | 9/2012 |
| WO | WO 2012/118829 A2 | 9/2012 |
| WO | WO 2012/155203 A1 | 11/2012 |
| WO | WO 2013/006608 A1 | 1/2013 |
| WO | WO 2013/006613 A1 | 1/2013 |
| WO | WO 2013/029009 A1 | 2/2013 |
| WO | WO 2013/063354 A1 | 5/2013 |
| WO | WO 2013/138073 A1 | 9/2013 |
| WO | WO 2013/138075 A1 | 9/2013 |
| WO | WO 2014/028847 A1 | 2/2014 |
| WO | WO 2014/134502 A1 | 9/2014 |
| WO | WO 2015/021382 A2 | 2/2015 |
| WO | WO 2016/010988 A1 | 1/2016 |
| WO | WO 2016/022170 A1 | 2/2016 |
| WO | WO 2016/160089 A1 | 10/2016 |
| WO | WO 2017/011031 A1 | 1/2017 |

OTHER PUBLICATIONS

McHale et al. "In Vitro Nail Penetration of Nitric Oxide-releasing Formulations for the Topical Treatment of Onychomycosis" *Microbe Poster*—www.novantherapeutics.com (1 page) (2016).

Novan, Inc. Press Release "Novan Announces First Patient Dosed in Phase 2 Anti-Fungal Program" http://investors.novan.com (4 pages) (Jul. 21, 2016).

De Groote et al. "NO Inhibitions: Antimicrobial Properties of Nitric Oxide" *Clinical Infectious Diseases* 21(Suppl. 2):S162-S165 (1995).

International Search Report and the Written Opinion of the International Searching Authority corresponding to International Patent Application No. PCT/US2015/040319 (13 pages) (dated Oct. 1, 2015).

International Search Report and the Written Opinion of the International Searching Authority corresponding to International Patent Application No. PCT/US2016/013246 (12 pages) (dated Mar. 17, 2016).

(56) References Cited

OTHER PUBLICATIONS

Kai et al. "Management of Acral Lentiginous Melanoma" https://www.intechopen.com/books/melanoma-from-early-detection-to-treatment/management-of-acral-lentiginous-melanoma (6 pages total; no pagination) (2013).

* cited by examiner

NITRIC OXIDE RELEASING NAIL COATING COMPOSITIONS, NITRIC OXIDE RELEASING NAIL COATINGS, AND METHODS OF USING THE SAME

RELATED APPLICATION INFORMATION

This application claims the benefit of U.S. Provisional Patent Application Ser. No. 62/024,200, filed Jul. 14, 2014, the disclosure of which is incorporated herein by reference in its entirety.

FIELD OF THE INVENTION

The present invention relates to nail coating compositions and/or coatings that may release nitric oxide. The present invention also relates to methods of using nail coating compositions and/or coatings, including methods of using nitric oxide-releasing nail coating compositions and/or coatings to treat fungal infections of the nail and/or nail conditions.

BACKGROUND

The current treatment modes for fungal infections of the nail typically include oral therapy, topical therapy, or a combination of the two. Oral therapies often involve a long treatment period due to low bioavailability of the drug at the sight of action, as well as a high potential for systemic adverse effects.

Topical therapies tend to be advantageous over oral treatment due to application of the drug directly to the infected site and minimal systemic adverse effects associated with the treatment. However, some drawbacks of many antifungal topical formulations include that drug penetration to the nail bed may be inhibited due to significant lag times in nail penetration, the inherent complex structure of the nail and the short time period in which the formulation remains on the nail.

The present invention may address previous shortcomings in the art by providing compositions and/or methods of treating and/or preventing nail disorders and/or diseases (e.g., fungal infections) and/or by providing compositions and/or methods of improving the appearance of a nail.

SUMMARY OF THE INVENTION

It is noted that aspects described with respect to one embodiment may be incorporated in different embodiments although not specifically described relative thereto.

Provided according to embodiments of the invention are nitric oxide (NO)-releasing nail coating compositions and/or coatings. In some embodiments, a NO-releasing nail coating composition and/or coating may be in the form of a film. In some embodiments, a NO-releasing nail coating may be formed from a NO-releasing nail coating composition. In some embodiments, a NO-releasing nail coating composition may be in the form of a nail lacquer, a paste, a cream, a gel, and/or an ointment.

In some embodiments, the NO-releasing nail coating and/or coating composition may include at least one NO-releasing compound. In some embodiments, the at least one NO-releasing compound releases NO upon reaction with a proton source. In some embodiments, the proton source is a proton donor (e.g., water). In some embodiments, the at least one NO-releasing compound includes NO-releasing co-condensed silica.

Provided according to some embodiments are NO-releasing nail lacquers. The NO-releasing nail lacquers may include at least one NO-releasing compound, such as, for example, at least one NO-releasing compound that releases NO upon reaction with a proton source (e.g., a proton donor, such as, water). In some embodiments, the at least one NO-releasing compound includes NO-releasing co-condensed silica. In some embodiments, the NO-releasing nail lacquers further include at least one hydrophilic polymer, at least one film forming polymer, and/or an organic solvent.

Further provided according to some embodiments is a one component NO-releasing nail coating composition. The one component NO-releasing nail coating composition may be in the form of a NO-releasing nail lacquer, paste, film, gel, cream, and/or ointment.

In some embodiments, a two component NO-releasing nail coating system is provided. In some embodiments, one component of the two component NO-releasing nail coating system may include a NO-releasing coating composition (e.g., a NO-releasing nail lacquer, paste, and/or ointment) and the other component of the two component NO-releasing nail coating system may include a composition including a proton source (e.g., a proton donor, such as, water). In some embodiments, the composition including a proton source is a hydrogel.

In addition, provided according to some embodiments of the invention are methods of treating a fungal infection of the nail and/or a nail condition comprising contacting a nail with a NO-releasing nail coating composition (e.g., a NO-releasing nail lacquer, paste, and/or ointment) according to an embodiment of the invention.

In some embodiments, a method of treating a fungal infection of the nail and/or a nail condition may comprise providing on a nail a NO-releasing nail coating according to an embodiment of the invention.

The foregoing and other aspects of the present invention will now be described in more detail with respect to other embodiments described herein. It should be appreciated that the invention can be embodied in different forms and should not be construed as limited to the embodiments set forth herein. Rather, these embodiments are provided so that this disclosure will be thorough and complete, and will fully convey the scope of the invention to those skilled in the art.

DETAILED DESCRIPTION

The present invention will now be described more fully hereinafter. This invention may, however, be embodied in different forms and should not be construed as limited to the embodiments set forth herein. Rather, these embodiments are provided so that this disclosure will be thorough and complete, and will fully convey the scope of the invention to those skilled in the art.

The terminology used in the description of the invention herein is for the purpose of describing particular embodiments only and is not intended to be limiting of the invention. As used in the description of the invention and the appended claims, the singular forms "a", "an" and "the" are intended to include the plural forms as well, unless the context clearly indicates otherwise.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the present application and relevant art and should not be interpreted in an idealized or overly formal sense unless expressly so defined herein. The terminology used in the description of the invention herein is for the purpose of describing particular embodiments only and is not intended to be limiting of the invention. All publications, patent applications, patents and other references mentioned herein are incorporated by reference in their entirety. In case of a conflict in terminology, the present specification is controlling.

Also as used herein, "and/or" refers to and encompasses any and all possible combinations of one or more of the associated listed items, as well as the lack of combinations when interpreted in the alternative ("or").

Unless the context indicates otherwise, it is specifically intended that the various features of the invention described herein can be used in any combination. Moreover, the present invention also contemplates that in some embodiments of the invention, any feature or combination of features set forth herein can be excluded or omitted. To illustrate, if the specification states that a complex comprises components A, B and C, it is specifically intended that any of A, B or C, or a combination thereof, can be omitted and disclaimed.

As used herein, the transitional phrase "consisting essentially of" (and grammatical variants) is to be interpreted as encompassing the recited materials or steps "and those that do not materially affect the basic and novel characteristic(s)" of the claimed invention. See, In re Herz, 537 F.2d 549, 551-52, 190 U.S.P.Q. 461, 463 (CCPA 1976) (emphasis in the original); see also MPEP § 2111.03. Thus, the term "consisting essentially of" as used herein should not be interpreted as equivalent to "comprising."

The term "about," as used herein when referring to a measurable value, such as, for example, an amount or concentration and the like, is meant to encompass variations of up to ±20% of the specified value, such as, but not limited to, ±10%, ±5%, ±1%, ±0.5%, or even ±0.1% of the specified amount, as well as the specified value. For example, "about X" where X is the measurable value, is meant to include X as well as variations of ±20%, ±10%, ±5%, ±1%, ±0.5%; or even ±0.1% of X. A range provided herein for a measureable value may include any other range and/or individual value therein.

As used herein the term "alkyl" refers to $C_{1-20}$ inclusive, linear (i.e., "straight-chain"), branched, or cyclic, saturated or at least partially and in some cases fully unsaturated (i.e., alkenyl and alkynyl) hydrocarbon chains, including for example, methyl, ethyl, propyl, isopropyl, butyl, isobutyl, tert-butyl, pentyl, hexyl, octyl, ethenyl, propenyl, butenyl, pentenyl, hexenyl, octenyl, butadienyl, propynyl, butynyl, pentynyl, hexynyl, heptynyl, and allenyl groups. "Branched" refers to an alkyl group in which a lower alkyl group, such as methyl, ethyl or propyl, is attached to a linear alkyl chain. Exemplary branched alkyl groups include, but are not limited to, isopropyl, isobutyl, tert-butyl. "Lower alkyl" refers to an alkyl group having 1 to about 8 carbon atoms (i.e., a $C_{1-8}$ alkyl), e.g., 1, 2, 3, 4, 5, 6, 7, or 8 carbon atoms. "Higher alkyl" refers to an alkyl group having about 10 to about 20 carbon atoms, e.g., 10, 11, 12, 13, 14, 15, 16, 17, 18, 19, or 20 carbon atoms. In certain embodiments, "alkyl" refers, in particular, to $C_{1-5}$ straight-chain alkyls. In other embodiments, "alkyl" refers, in particular, to $C_{1-5}$ branched-chain alkyls.

Alkyl groups may optionally be substituted (a "substituted alkyl") with one or more alkyl group substituents, which may be the same or different. The term "alkyl group substituent" includes but is not limited to alkyl, substituted alkyl, halo, arylamino, acyl, hydroxyl, aryloxyl, alkoxyl, alkylthio, arylthio, aralkyloxyl, aralkylthio, carboxyl, alkoxycarbonyl, oxo, and cycloalkyl. There may be optionally inserted along the alkyl chain one or more oxygen, sulfur or substituted or unsubstituted nitrogen atoms, wherein the nitrogen substituent is hydrogen, lower alkyl (also referred to herein as "alkylaminoalkyl"), or aryl.

Thus, as used herein, the term "substituted alkyl" includes alkyl groups, as defined herein, in which one or more atoms or functional groups of the alkyl group are replaced with another atom or functional group, including for example, alkyl, substituted alkyl, halogen, aryl, substituted aryl, alkoxyl, hydroxyl, nitro, amino, alkylamino, dialkylamino, sulfate, and mercapto.

The term "aryl" is used herein to refer to an aromatic substituent that may be a single aromatic ring, or multiple aromatic rings that are fused together, linked covalently, or linked to a common group, such as, but not limited to, a methylene or ethylene moiety. The common linking group also may be a carbonyl, as in benzophenone, or oxygen, as in diphenylether, or nitrogen, as in diphenylmine. The term "aryl" specifically encompasses heterocyclic aromatic compounds. The aromatic ring(s) may comprise phenyl, naphthyl, biphenyl, diphenylether, diphenylamine and benzophenone, among others. In particular embodiments, the term "aryl" means a cyclic aromatic comprising about 5 to about 10 carbon atoms, e.g., 5, 6, 7, 8, 9, or 10 carbon atoms, and including 5- and 6-membered hydrocarbon and heterocyclic aromatic rings.

The aryl group may be optionally substituted (a "substituted aryl") with one or more aryl group substituents, which may be the same or different, wherein "aryl group substituent" includes alkyl, substituted alkyl, aryl, substituted aryl, aralkyl, hydroxyl, alkoxyl, aryloxyl, aralkyloxyl, carboxyl, acyl, halo, nitro, alkoxycarbonyl, aryloxycarbonyl, aralkoxycarbonyl, acyloxyl, acylamino, aroylamino, carbamoyl, alkylcarbamoyl, dialkylcarbamoyl, arylthio, alkylthio, alkylene, and —NR$^1$R", wherein R$^1$ and R" may each be independently hydrogen, alkyl, substituted alkyl, aryl, substituted aryl, and aralkyl.

Thus, as used herein, the term "substituted aryl" includes aryl groups, as defined herein, in which one or more atoms or functional groups of the aryl group are replaced with another atom or functional group, including for example, alkyl, substituted alkyl, halogen, aryl, substituted aryl, alkoxyl, hydroxyl, nitro, amino, alkylamino, dialkylamino, sulfate, and mercapto. Specific examples of aryl groups include, but are not limited to, cyclopentadienyl, phenyl, furan, thiophene, pyrrole, pyran, pyridine, imidazole, benzimidazole, isothiazole, isoxazole, pyrazole, pyrazine, triazine, pyrimidine, quinoline, isoquinoline, indole, carbazole, and the like.

"Cyclic" and "cycloalkyl" refer to a non-aromatic mono- or multicyclic ring system of about 3 to about 10 carbon atoms, e.g., 3, 4, 5, 6, 7, 8, 9, or 10 carbon atoms. The cycloalkyl group may be optionally partially unsaturated. The cycloalkyl group also may be optionally substituted with an alkyl group substituent as defined herein, oxo, and/or alkylene. There may be optionally inserted along the cyclic alkyl chain one or more oxygen, sulfur or substituted or unsubstituted nitrogen atoms, wherein the nitrogen substituent is hydrogen, alkyl, substituted alkyl, aryl, or substituted aryl, thus providing a heterocyclic group. Representative monocyclic cycloalkyl rings include cyclopentyl, cyclohexyl, and cycloheptyl. Multicyclic cycloalkyl rings include adamantyl, octahydronaphthyl, decalin, camphor, camphane, and noradamantyl.

"Alkoxyl" refers to an alkyl-O— group wherein alkyl is as previously described. The term "alkoxyl" as used herein may refer to, for example, methoxyl, ethoxyl, propoxyl, isopropoxyl, butoxyl, f-butoxyl, and pentoxyl. The term "oxyalkyl" may be used interchangeably with "alkoxyl". In some embodiments, the alkoxyl has 1, 2, 3, 4, or 5 carbons.

"Aralkyl" refers to an aryl-alkyl group wherein aryl and alkyl are as previously described, and included substituted aryl and substituted alkyl. Exemplary aralkyl groups include, but are not limited to, benzyl, phenylethyl, and naphthylmethyl.

"Alkylene" refers to a straight or branched bivalent aliphatic hydrocarbon group having from 1 to about 20 carbon atoms, e.g., 1, 2, 3, 4, 5, 6, 7, 8, 9, 10, 11, 12, 13, 14, 15, 16, 17, 18, 19, or 20 carbon atoms. The alkylene group may be straight, branched or cyclic. The alkylene group also may be optionally unsaturated and/or substituted with one or more "alkyl group substituents." There may be optionally inserted along the alkylene group one or more oxygen, sulfur or substituted or unsubstituted nitrogen atoms (also referred to herein as "alkylaminoalkyl"), wherein the nitrogen substituent is alkyl as previously described. Exemplary alkylene groups include, but are not limited to, methylene ($-CH_2-$); ethylene ($-CH_2-CH_2-$); propylene ($-(CH_2)_3-$); cyclohexylene ($-C_6H_{10}-$); $-CH=CH-CH=CH-$; $-CH=CH-CH_2-$; wherein each of q and r is independently an integer from 0 to about 20, e.g., 0, 1, 2, 3, 4, 5, 6, 7, 8, 9, 10, 11, 12, 13, 14, 15, 16, 17, 18, 19, or 20, and R is hydrogen or lower alkyl; methylenedioxyl ($-O-CH_2-O-$); and ethylenedioxyl ($-O-(CH_2)_2-O-$). An alkylene group may have about 2 to about 3 carbon atoms and may further have 6-20 carbons.

"Arylene" refers to a bivalent aryl group. An exemplary arylene is phenylene, which may have ring carbon atoms available for bonding in ortho, meta, or para positions with regard to each other, i.e., respectively. The arylene group may also be napthylene. The arylene group may be optionally substituted (a "substituted arylene") with one or more "aryl group substituents" as defined herein, which may be the same or different.

"Aralkylene" refers to a bivalent group that contains both alkyl and aryl groups. For example, aralkylene groups may have two alkyl groups and an aryl group (i.e., -alkyl-aryl-alkyl-), one alkyl group and one aryl group (i.e., -alkyl-aryl-) or two aryl groups and one alkyl group (i.e., -aryl-alkyl-aryl-).

The term "amino" and "amine" refer to nitrogen-containing groups such as $NR_3$, $NH_3$, $NHR_2$, and $NH_2R$, wherein R may be alkyl, branched alkyl, cycloalkyl, aryl, alkylene, arylene, aralkylene. Thus, "amino" as used herein may refer to a primary amine, a secondary amine, or a tertiary amine. In some embodiments, one R of an amino group may be a cation stabilized diazeniumdiolate (i.e., $NONO^-X^+$).

The terms "cationic amine" and "quaternary amine" refer to an amino group having an additional (i.e., a fourth) group, for example a hydrogen or an alkyl group bonded to the nitrogen. Thus, cationic and quaternary amines carry a positive charge.

The term "alkylamine" refers to the -alkyl-$NH_2$ group.

The term "carbonyl" refers to the $-(C=O)-$ group.

The term "carboxyl" refers to the $-COOH$ group and the term "carboxylate" refers to an anion formed from a carboxyl group, i.e., $-COO^-$.

The terms "halo", "halide", or "halogen" as used herein refer to fluoro, chloro, bromo, and iodo groups.

The term "hydroxyl" and "hydroxy" refer to the —OH group.

The term "hydroxyalkyl" refers to an alkyl group substituted with an —OH group.

The term "mercapto" or "thio" refers to the —SH group. The term "silyl" refers to groups comprising silicon atoms (Si).

As used herein the term "alkoxysilane" refers to a compound comprising one, two, three, or four alkoxy groups bonded to a silicon atom. For example, tetraalkoxysilane refers to $Si(OR)_4$, wherein R is alkyl. Each alkyl group may be the same or different. An "alkylsilane" refers to an alkoxysilane wherein one or more of the alkoxy groups has been replaced with an alkyl group. Thus, an alkylsilane comprises at least one alkyl-Si bond. The term "fluorinated silane" refers to an alkylsilane wherein one of the alkyl groups is substituted with one or more fluorine atoms. The term "cationic or anionic silane" refers to an alkylsilane wherein one of the alkyl groups is further substituted with an alkyl substituent that has a positive (i.e., cationic) or a negative (i.e. anionic) charge, or may become charged (i.e., is ionizable) in a particular environment (i.e., in vivo).

The term "silanol" refers to a Si—OH group.

Provided according to some embodiments of the invention are nail coating compositions and/or coatings that include at least one nitric oxide (NO)-releasing compound (i.e., NO-releasing nail coating compositions and/or coatings). A nail coating composition as described herein may provide and/or form a nail coating as described herein on a nail of a subject after topical application. A nail coating composition of the present invention may or may not change in form (e.g., from a liquid to another form, such as a solid or semi-solid film) upon and/or after application to a subject to provide a nail coating of the present invention. A nail coating composition and/or nail coating of the present invention may release NO onto and/or into a nail of a subject to which the composition and/or coating is in contact with and/or onto and/or into skin under and/or around the nail. In some embodiments of the invention, the at least one NO-releasing compound included in the composition and/or coating may release NO upon reaction with a proton source, such as, but not limited to, water. In some embodiments, the at least one NO-releasing compound includes a diazeniumdiolate functional group.

Any suitable NO-releasing compound may be used in a nail coating composition and/or coating according to embodiments of the invention. Nitric oxide may be released from the NO-releasing compound by any suitable mechanism, including via reaction with a proton source (e.g., a proton donor, such as, water) and/or thermal degradation. Examples of NO-releasing functional groups that may be included in the NO-releasing compound include, but are not limited to, diazeniumdiolate, nitrosamine, hydroxyl nitrosamine, nitrosothiol, hydroxyl amine, hydroxyurea, metal nitrosyl complexes, and any combination thereof. Other NO-releasing functional groups that are capable of releasing nitric oxide in a therapeutic manner in a one component and/or two component nail coating composition and/or coating may also be utilized.

The NO-releasing compound may be a small molecule, oligomer, macromolecule and/or polymer and may be in any suitable physical form, including, but not limited to, particles, gels, hydrogels, films, liquids, and the like. In some embodiments, the nitric oxide-releasing compound includes diazeniumdiolate-functionalized polysiloxane macromolecules as described below. Other examples of NO-releasing compounds include NO-releasing zeolites as described in United States Patent Application Publication Nos. 2006/0269620 or 2010/0331968; NO-releasing metal organic frameworks (MOFs) as described in United States Patent Application Publication Nos. 2010/0239512 or 2011/0052650; NO-releasing multi-donor compounds as described in U.S. Patent Application Publication No. 2014/0171395; NO-releasing dendrimers or metal structures as described in U.S. Patent Application Publication No. 2009/0214618; nitric oxide releasing coatings as described in U.S. Patent Application Publication No. 2011/0086234; and compounds as described in U.S. Patent Application Publication No. 2010/0098733. The disclosures of each of the references in this paragraph are incorporated herein by reference in their entirety. Additionally, NO-releasing macromolecules may be fabricated as described in International Publication No. WO 2012/100174, the disclosure of which is incorporated herein by reference in its entirety.

In some embodiments, the NO-releasing compound includes a macromolecule that includes an NO donor group. A "macromolecule" is defined herein as any compound that has a molecular weight of 500 daltons or greater. Any suitable macromolecule may be used, including crosslinked or non-crosslinked polymers, dendrimers, metallic compounds, organometallic compounds, inorganic-based compounds, and other macromolecular scaffolds. In some embodiments, the macromolecule has a nominal diameter ranging from about 0.1 nm to about 100 µm and may comprise the aggregation of two or more macromolecules, whereby the macromolecular structure is further modified with an NO donor group.

In some embodiments, the NO-releasing macromolecule includes diazeniumdiolate-functionalized co-condensed silica. The term "diazeniumdiolate-functionalized co-condensed silica" refers to co-condensed polysiloxane macromolecules functionalized with diazeniumdiolate, such as the NO-releasing particles described in U.S. Patent Application Publication No. 2009/0214618, the disclosure of which is incorporated by reference herein in its entirety. Such particles may be prepared by methods described therein.

In some embodiments, the diazeniumdiolate-functionalized co-condensed silica may be formed from an aminoalkoxysilane by a pre-charging method, and the co-condensed siloxane network may be synthesized from the condensation of a silane mixture that includes an alkoxysilane and the aminoalkoxysilane to form a nitric oxide donor modified co-condensed siloxane network. As used herein, the "pre-charging method" means that aminoalkoxysilane is "pretreated" or "precharged" with nitric oxide prior to the co-condensation with alkoxysilane. In some embodiments, the precharging nitric oxide may be accomplished by chemical methods. In another embodiment, the "pre-charging" method may be used to create co-condensed siloxane networks and materials more densely functionalized with NO-donors.

The co-condensed siloxane network may be silica particles with a uniform size, a collection of silica particles with a variety of size, amorphous silica, fumed silica, a nanocrystalline silica, ceramic silica, colloidal silica, a silica coating, a silica film, organically modified silica, mesoporous silica, silica gel, bioactive glass, or any suitable form or state of silica.

In some embodiments, the alkoxysilane is a tetraalkoxysilane having the formula $Si(OR)_4$, wherein R is an alkyl group. The R groups may be the same or different. In some embodiments the tetraalkoxysilane is selected as tetramethyl orthosilicate (TMOS) or tetraethyl orthosilicate (TEOS). In some embodiments, the aminoalkoxysilane has the formula: $R''—(NH—R')_n—Si(OR)_3$, wherein R is alkyl, R' is alkylene, branched alkylene, or aralkylene, n is 1 or 2, and R" is selected from the group consisting of alkyl, cycloalkyl, aryl, and alkylamine.

In some embodiments, the aminoalkoxysilane may be selected from N-(6-aminohexyl)aminopropyltrimethoxysilane (AHAP3); N-(2-aminoethyl)-3-aminopropyltrimethoxysilane (AEAP3); (3-trimethoxysilylpropyl)di-ethylenetriamine (DET3); (aminoethylaminomethyl)phenethyltrimethoxysilane (AEMP3); [3-(methylamino)propyl]trimethoxysilane (MAP3); N-butylaminopropyltrimethoxysilane(n-BAP3); t-butylaminopropyltrimethoxysilane(t-BAP3); N-ethylaminoisobutyltrimethoxysilane(EAiB3); N-phenylamino-propyltrimethoxysilane (PAP3); and N-cyclohexylaminopropyltrimethoxysilane (cHAP3).

In some embodiments, the aminoalkoxysilane has the formula: $NH [R'—Si(OR)_3]_2$, wherein R is alkyl and R' is alkylene. In some embodiments, the aminoalkoxysilane may be selected from bis(3-triethoxysilylpropyl)amine, bis-[3-(trimethoxysilyl)propyl]amine and bis-[(3-trimethoxysilyl)propyl]ethylenediamine.

In some embodiments, as described herein above, the aminoalkoxysilane is precharged for NO-release and the amino group is substituted by a diazeniumdiolate. Therefore, in some embodiments, the aminoalkoxysilane has the formula: $R''—N(NONO^-X^+)—R'—Si(OR)_3$, wherein R is alkyl or silyl, R' is alkylene or aralkylene, R" is alkyl or alkylamine, and $X^+$ is a cation selected from the group consisting of $Na^+$, $K^+$, $Cs^+$, $Li^+$, $NH_4^+$, or other quaternary ammonium cation.

In some embodiments of the invention, the diazeniumdiolate-functional aminoalkoxysilane may be $O^2$-protected prior to the preparation of the nitric oxide releasing macromolecules. Such $O^2$-protected diazeniumdiolate functional aminoalkoxysilanes may have the formula: $R''—N(NONO—R''')—R'—Si(OR)_3$, wherein each R is independently H, alkyl or substituted alkyl, R' is substituted or unsubstituted alkylene, substituted or unsubstituted arylene, substituted or unsubstituted alkylarylene or substituted or unsubstituted arylalkylene, R" is H, alkyl or substituted alkyl and R''' is a protecting group that imparts enzymatic, photolytic, or thiolation triggering mechanisms. Such protecting groups are known to those skilled in the art of forming $O^2$-protected diazeniumdiolates.

The chemical composition of the siloxane network, (e.g., amount or the chemical composition of the aminoalkoxysilane), the porosity of the silica network within the macromolecular structure, the size of the co-condensed silica particles, and the nitric oxide charging conditions (e.g., the solvent and base) may be varied to optimize the amount and duration of nitric oxide release. Thus, in some embodiments, the composition of the silica particles may be modified to regulate the half-life of NO release from silica particles with half-lives of nitric oxide release ranging from slow, defined by $t_{1/2}$ values greater than about 60 minutes to fast, defined by $t_{1/2}$ values ranging from about 30 seconds to about 10 minutes (at physiological conditions –37° C. and pH=7.4).

In some embodiments of the invention, the co-condensed siloxane network of nitric oxide releasing silica particles is formed from at least one additional silane that modifies surface charge and/or hydrophilicity/hydrophobicity of the co-condensed silica product which affect the octanol/water partition coefficient of the macromolecular delivery vehicle. These parameters control the route of skin penetration, depth of penetration, and diffusion of the diazeniumdiolate-modified polysiloxane macromolecules into the aqueous solution. Any suitable alkoxysilane that may impart surface charge to the diazeniumdiolate-modified polysiloxane macromolecule may be used. Thus, in some embodiments, the additional alkoxysilane may include a cationic alkoxysilane such as (2-N-benyzlaminoethyl)-3-aminopropyl-trimethoxysilane, hydrocholoride; bis(methoxyethyl)-3-trimethoxysilylpropyl-ammonium chloride; N—N-didecyl-N-methyl-N-(3-trimethoxysilyl)ammonium chloride; N-trimethyoxysilyl-propyl-N,N,N-trimethyl ammonium chloride; octadecylbis (triethoxysilylpropyl)-ammonium chloride; and octadecyldimethyl(3-trimethoxysilylpropyl)ammonium chloride. In some embodiments, the additional alkoxysilane may include an anionic alkoxysilanes such as 3-trihydroxysilylpropylmethyl phosphonate, sodium salt and carboxy-ethylsilanetriol, sodium salt.

Any suitable alkoxysilane that may impart hydrophilic properties to the diazeniumdiolate-modified polysiloxane macromolecule may be used. Alkoxysilanes containing repeat poly(ethylene)oxy groups may be used to increase the wetability of the NO-releasing particles thereby helping to improve biocompatibility upon topical application and also enhance the rate of water uptake into the co-condensed siloxane network. Surface hydrophilicity may thus be utilized to enhance the NO-release kinetics of the diazeniumdiolated aminoalkoxysilane derivatives. Therefore, in some embodiments, the multifunctional alkoxysilane may include a hydrophilic silane such as N-triethoxysilylpropyl)-O-polyethyleneoxide urethane; N-3-[amino(polypropylenoxy)] aminopropyltrimethoxysilane; bis-[3-(triethoxysilyl-propoxy)-2-hydroxypropoxy]polyethylene oxide; bis(3-triethoxysilylpropyl)polyethylene oxide (25-30); [hydroxy (polyethyleneoxy)propyl]-triethoxysilane; and 2-[methoxy (polyethyleneoxy)propyl]-trimethoxysilane.

Any suitable alkoxysilane that may impart hydrophobic properties to the diazeniumdiolate-modified polysiloxane macromolecule may be used. Hydrophobic silanes are known to those skilled in the art to increase lipophilicity of particle surfaces. In some embodiments, the additional alkoxysilane may include linear alkyl, branched and cyclic alkylalkoxysilanes having at least three carbon atoms, substituted and unsubstituted phenyl alkoxysilanes, and fluorinated alkoxysilanes. Exemplary fluoroalkoxysilanes may include heptadecafluoro-1,1,2-2-tetrahydrodecyl)triethoxysilane, (3,3,3-trifluoropropyl)trimethoxysilane, (perfluoroalkyl)ethyltriethoxysilane, nonafluorohexyltrimethoxysilane, nonafluorohexyltriethoxysilane, (tridecafluoro-1,1,2,2-tetrahydrooctyl)triethoxysilane, and (tridecafluoro-1,1,2,2-tetrahydrooctyl)trimethoxysilane.

The hydrophilicity of the diazeniumdiolate-functionalized polysiloxane macromolecules may be assessed by the use of a water/octanol partition coefficient. See *Octanol-Water Partition Coefficients: Fundamentals and Physical Chemistry, Vol. 2 of Wiley Series in Solution Chemistry.* Chichester: John Wiley & Sons Ltd. (1997), which is herein incorporated by reference in its entirety. For example, hydrophobic diazeniumdiolate-functionalized polysiloxane macromolecules may have a water/octanol partition coefficient in a range from about, 0.1 to about 7, and hydrophilic diazeniumdiolate-functionalized polysiloxane macromolecules may have a water/octanol partition coefficient in a range from about −2 to about 0.

In some embodiments of the invention, the hydrodynamic radius of the diazeniumdiolate-functionalized co-condensed silica particles is in a range of about 10 nm to about 100 µm. The particular size, sizes or range of sizes may be selected to maximize nail penetration and/or enhance nitric oxide delivery to skin structures beneath the nail. The size(s) of the particle may also be selected based on the ability of the particle to provide substantially uniform coverage when suspended in the nail coating and/or nail coating composition. Additionally, the size(s) of the particles may also vary when other nitric oxide releasing materials are utilized. For example, a nitric oxide releasing dendrimer may be sized to penetrate the nail.

A NO-releasing compound may be present in a nail coating composition and/or nail coating according to embodiments of the invention at any suitable concentration. In some embodiments, a NO-releasing compound may be present in a nail coating composition and/or nail coating at a concentration sufficient to exert a therapeutic effect, including in some cases, an antimicrobial effect and/or an antimycotic effect. In some embodiments, a NO-releasing compound may be present in a nail coating composition and/or nail coating in a treatment effective and/or prevention effective amount.

In some embodiments, a nail coating composition and/or nail coating may comprise a NO-releasing compound and may store and/or release nitric oxide in an amount of about 0.05% to about 20% by weight of the nail coating composition and/or nail coating, such as, but not limited to, about 0.15% to about 2%, about 0.15% to about 1%, about 0.3% to about 1.2%, about 0.15% to about 6%, about 1% to about 10%, about 3% to about 6%, about 2% to about 20%, about 5% to about 15%, about 10% to about 20%, or about 1% to about 5% by weight of the nail coating composition and/or nail coating. In certain embodiments, a nail coating composition and/or nail coating of the present invention may comprise a NO-releasing compound and may store and/or release NO in an amount of about 0.15%, 0.3%, 0.6%, 0.9%, 1%, 1.25%, 1.5%, 1.75%, 2%, 2.25%, 2.5%, 2.75%, 3%, 3.25%, 3.5%, 3.75%, 4%, 4.25%, 4.5%, 4.75%, 5%, 5.25%, 5.5%, 5.75%, 6%, 6.25%, 6.5%, 6.75%, 7%, 7.25%, 7.5%, 7.75%, 8%, 8.25%, 8.5%, 8.75%, 9%, 9.25%, 9.5%, 9.75%, 10%, 10.25%, 10.5%, 10.75%, 11%, 11.25%, 11.5%, 11.75%, 12%, 12.25%, 12.5%, 12.75%, 13%, 13.25%, 13.5%, 13.75%, 14%, 14.25%, 14.5%, 14.75%, 15%, 15.25%, 15.5%, 15.75%, 16%, 16.25%, 16.5%, 16.75%, 17%, 17.25%, 17.5%, 17.75%, 18%, 18.25%, 18.5%, 18.75%, 19%, 19.25%, 19.5%, 19.75%, or 20% by weight of the nail coating composition and/or nail coating. The amount of nitric oxide released may be determined using real time in vitro release testing. In some embodiments, nitric oxide release may be determined using a chemiluminescent nitric oxide analyzer.

In some embodiments, a NO-releasing compound (e.g., a NO-releasing macromolecule) present in a nail coating composition and/or nail coating may be in the form of a nanoparticle. In some embodiments, the NO-releasing compound may be dissolved in (e.g., completely or partially) and/or suspended in the vehicle for the nail coating composition and/or nail coating, which may be in the form of a liquid, gel, cream, ointment, etc.

In some embodiments, at least one NO-releasing macromolecule may be present in a nail coating composition and/or nail coating. The at least one NO-releasing macromolecule may be present in a nail coating composition and/or nail coating according to embodiments of the invention at any suitable concentration. In some embodiments, NO-releasing macromolecules may be present in a nail coating composition and/or nail coating at a concentration sufficient to exert a therapeutic effect, including in some cases, an antimicrobial effect and/or an antimycotic effect. In some embodiments, a NO-releasing macromolecule may be present in a nail coating composition and/or nail coating in a treatment effective and/or prevention effective amount. For example, in some embodiments, the concentration of diazeniumdiolate-functionalized co-condensed silica in a nail coating composition (e.g., a nail lacquer) may be in a range from about 0.1% to about 70% by weight of the nail coating composition, and/or any range and/or individual value therein, such as, for example, about 0.1% to about 25% or about 0.1% to about 50% by weight of the nail coating composition. In some embodiments, a diazeniumdiolate-functionalized co-condensed silica may be present in a nail coating composition in an amount of about 0.1%, 0.25%, 0.5%, 0.75%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, or 70% by weight of the nail coating composition. Thus, upon and/or after topical application to a nail of a subject, the resulting nail coating may have a concentration of diazeniumdiolate-functionalized co-condensed silica in a range from about 0.1% to about 70% or more by weight of the coating, and/or any range and/or individual value therein.

As one of skill will recognize, the weight percentages for ingredients in a nail coating composition may be different than those of a coating resulting from the composition, such as, for example, due to drying and/or curing of the composition and/or evaporation of one or more solvents in the composition. In some embodiments, a weight percentage provided herein for an ingredient in a nail coating composition is based on the weight of the composition prior to drying and/or curing. In some embodiments, a weight percentage provided herein for an ingredient in a nail coating composition and/or coating is based on the weight of the composition and/or coating without the NO-releasing compound (i.e., the weight percentage for an ingredient may be based on the vehicle coating composition and/coating).

In some embodiments, the NO release may be tuned by adjusting the concentration of the NO-releasing macromolecules in the composition and/or coating and/or adjusting the NO loading (mol NO/g composition and/or coating) of the macromolecules therein to create the desired NO release profile.

In some embodiments, the final NO storage per milligram of the nail coating composition and/or nail coating may be in a range from about 1 nmol NO/mg composition and/or coating to about 2.5 µmol NO/mg composition and/or coating, or any range and/or individual value therein. In some embodiments, the NO storage per milligram of nail coating composition and/or nail coating is in a range from about 0.25 µmol NO/mg to about 5 µmol NO/mg, or any range and/or individual value therein. In some embodiments, the NO storage is about 0.1, 0.2, 0.3, 0.4, 0.5, 0.6, 0.7, 0.8, 0.9, 1, 1.5, 2, 2.5, 3, 3.5, 4, 4.5, or 5 µmol NO/mg, or any range and/or individual value therein.

In some embodiments of the invention, a NO-releasing nail coating composition and/or nail coating may include at least one film-forming polymer. Any suitable film-forming polymer may be used in a nail coating composition and/or nail coating of the present invention, and such polymers include film-forming polymers previously known and used in nail coating compositions and/or coatings, and those found to be useful as film-forming polymers in nail coating compositions and/or coatings. In some embodiments, the film-forming polymer has suitable adhesion to nail keratin (and/or skin) and/or forms water-insoluble and/or water-resistant films.

Examples of film-forming polymers that may be used in a nail coating composition and/or nail coating described herein, include, but are not limited to, cellulose derivatives such as ethyl cellulose, polyvinyl acetate, mixed polymers (or copolymers) of vinyl acetate with acrylic or methacrylic acid, copolymers of (meth)acrylic acid and (meth)acrylate esters, copolymers of (meth)acrylic acid esters with amino group and/or quaternary ammonium group-containing comonomers, nitrocellulose, methyl vinyl ether/maleic acid copolymer (e.g., Gantrez™ S-97), vinyl pyrrolidone/vinyl acetate copolymer (Plasdone™ S-630), poly N-vinylacetamide/sodium acrylate copolymer (PNVA), and the like. Further examples of film-forming polymers include, but are not limited to, Ethocel™ polymers, such as, for example, Ethocel™ STD-10P, ETHOCEL™ STD-7P, and ETHOCEL™ STD-20P from Colorcon/Dow, methacrylate polymers (e.g., EUDRAGIT® L, EUDRAGIT® S) and copolymers (e.g., EUDRAGIT® E, EUDRAGIT® RS, EUDRAGIT® RL), polyethylene, polyvinyl acetate and/or cellulose acetate.

A film-forming polymer may be used alone in a nail coating composition and/or nail coating or in a mixture with one or more (e.g., 1, 2, 3, 4, or more) different film-forming polymer(s). A film-forming polymer may be either water-soluble or water-insoluble, and, in some embodiments a mixture of both may be used in a nail coating composition and/or nail coating. A water-insoluble polymer may protect the nail and/or provide a stronger coating and/or film. A water-soluble polymer may allow controlled and/or limited amounts of water to penetrate the coating and/or film, thus aiding in the release of nitric oxide. The particular combination of film-forming polymers may depend on the desired release rate of nitric oxide and the particular nitric oxide-releasing compound incorporated in the nail coating composition and/or nail coating.

According to some embodiments of the invention, the concentration of a film-forming polymer in a nail coating composition and/or nail coating may be in a range of about 1% to about 25% by weight of the nail coating composition and/or nail coating, or any range and/or individual value therein, such as, for example, about 1% to about 10%, about 1% to about 15%, about 1% to about 5%, about 5% to about 25%, or about 10% to about 20% by weight of the nail coating composition and/or nail coating. In certain embodiments, a film-forming polymer may be present in a nail coating composition and/or nail coating in an amount of about 1%, 2%, 3%, 4%, 5%, 6%, 7%, 8%, 9%, 10%, 11%, 12%, 13%, 14%, 15%, 16%, 17%, 18%, 19%, or 20% by weight of the nail coating composition and/or nail coating or any range and/or individual value therein.

In some embodiments, a hydrophilic polymer may be present in a nail coating composition and/or nail coating of the present invention. Any suitable hydrophilic polymer may be used in embodiments described herein. As used herein, a hydrophilic polymer is one that will absorb an amount of water (dependent on structure and molecular weight) and form a network around the water molecules creating a hydrogel without dissolving the polymer structure. Example hydrophilic polymers include, but are not limited to, hydroxypropyl methyl cellulose (e.g., METHOCEL®), hydroxypropyl cellulose (e.g., KLUCEL®), methylcellulose, polyvinylpyrrolidone polymer (PVP) and copolymers (e.g., KOLLIDON®), sodium carboxy methylcellulose and/or polyvinyl alcohol.

According to some embodiments of the invention, the concentration of a hydrophilic polymer in a nail coating composition and/or nail coating may be in a range of about 1% to about 15% by weight of the nail coating composition and/or nail coating, or any range and/or individual value therein, such as, for example, about 2% to about 8%, about 1% to about 5%, about 5% to about 10%, or about 5% to about 15% by weight of the nail coating composition and/or nail coating. In certain embodiments, a hydrophilic polymer may be present in a nail coating composition and/or nail coating in an amount of about 1%, 2%, 3%, 4%, 5%, 6%, 7%, 8%, 9%, 10%, 11%, 12%, 13%, 14%, or 15% by weight of the nail coating composition and/or nail coating or any range and/or individual value therein.

In some embodiments, an organic solvent may be present in a nail coating composition and/or nail coating of the present invention. Any suitable organic solvent may be used in embodiments described herein. Examples of organic solvents include, but are not limited to, hydrocarbons, halogenated hydrocarbons, alcohols, ethers, ketones and esters customary in cosmetics. In some embodiments, the organic solvent may be an acetic esters of monohydric alcohols (e.g., ethyl acetate, n-butyl acetate, etc.), that may be mixed with an aromatic hydrocarbon such as, for example, toluene and/or alcohols such as ethanol or isopropanol and/or aliphatic sulfoxides and sulfones such as, for example, dimethyl sulfoxide or sulfolane. Further examples of organic solvents include acetone, ethyl acetate, ethyl alcohol, denatured alcohol and/or isopropyl alcohol.

The type and/or quantity of the organic solvent(s) may be important for determining the drying time, ease of spreading and/or other properties of the composition and/or coating. In some embodiments of the invention, the organic solvent(s) may be anhydrous or substantially anhydrous, in order to prevent water reactive NO-releasing functional groups from releasing NO prior to application on a nail and/or skin surrounding the nail.

According to some embodiments of the invention, the concentration of an organic solvent in a nail coating composition and/or nail coating may be in a range of about 30% to about 99% by weight of the nail coating composition and/or nail coating, or any range and/or individual value therein, such as, for example, about 30% to about 50%, about 30% to about 80%, about 50% to about 99%, about 75% to about 99%, or about 80% to about 99% by weight of the nail coating composition and/or nail coating. In certain embodiments, an organic solvent may be present in a nail coating composition and/or nail coating in an amount of about 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% by weight of the nail coating composition and/or nail coating or any range and/or individual value therein.

A nail coating composition and/or nail coating according to embodiments of the invention may also contain additives common in cosmetics. Examples include, but are not limited to, plasticizers (e.g., trimethyl pentanyl diisobutyrate, triphenyl phosphate, and/or those based on phthalates or camphor), emollients (e.g., isopropyl palmitate), colorants, pigments, perlescent agents, thickening agents (e.g., stearalkonium hectorite and/or cetyl alcohol), adhesive agents, sedimentation retardants, sulfonamide resins, silicates, antioxidants, perfumes, wetting agents (e.g., sodium dioctylsulfosuccinate), lanolin derivatives, sunscreen agents (e.g., 2-hydroxy-4-methoxybenzophenone), substances having antibacterial activity, and/or substances with a keratolytic and/or keratoplastic action (e.g., ammonium sulfite, esters and salts of thioglycolic acid, urea, allantoin, enzymes and/or salicylic acid).

One or more additives may be present in a nail coating composition and/or nail coating in a concentration in a range from about 0.01% to about 20% by weight of the nail coating composition and/or nail coating, or any range and/or individual value therein, such as, for example, about 0.05% to about 1%, about 1% to about 20%, about 1% to about 10%, about 1% to about 5%, or about 5% to about 15% by weight of the nail coating composition and/or nail coating. In certain embodiments, one or more additives may be present in a nail coating composition and/or nail coating in an amount of about 0.01%, 0.02%, 0.03%, 0.04%, 0.05%, 0.06%, 0.07%, 0.08%, 0.09%, 0.1%, 0.2%, 0.3%, 0.4%, 0.5%, 0.6%, 0.7%, 0.8%, 0.9%, 1%, 2%, 3%, 4%, 5%, 6%, 7%, 8%, 9%, 10%, 11%, 12%, 13%, 14%, 15%, 16%, 17%, 18%, 19%, or 20% by weight of the nail coating composition and/or nail coating or any range and/or individual value therein.

In some embodiments, a nail coating composition (e.g., a nail lacquer) may comprise a NO-releasing compound in an amount of about 0.1% to about 70% by weight of the nail coating composition, a film-forming polymer in an amount of about 1% to about 25% by weight of the nail coating composition, an organic solvent in an amount of about 30% to about 99% by weight of the nail coating composition, optionally a hydrophilic polymer in an amount of about 1% to about 15% by weight of the nail coating composition, and optionally one or more additives (e.g., a plasticizer, thickening agent, antioxidant, colorant, pigment, etc.) each optionally present in an amount of about 0.01% to about 20% by weight of the nail coating composition. In some embodiments, the NO-releasing compound may be present in an amount of about 0.1% to about 50% by weight of the nail coating composition.

In some embodiments, a nail coating composition (e.g., a nail lacquer) may comprise a NO-releasing compound in an amount of about 0.1% to about 50% by weight of the nail coating composition, a film-forming polymer in an amount of about 1% to about 15% by weight of the nail coating composition, an organic solvent in an amount of about 65% to about 99% by weight of the nail coating composition, optionally a hydrophilic polymer in an amount of about 1% to about 15% by weight of the nail coating composition, and optionally one or more additives (e.g., a plasticizer, thickening agent, antioxidant, colorant, pigment, etc.) each optionally present in an amount of about 0.01% to about 10% by weight of the nail coating composition. In some embodiments, the NO-releasing compound may be present in an amount of about 0.1% to about 25% by weight of the nail coating composition.

In some embodiments, a nail coating composition (e.g., a nail paste and/or ointment) may comprise a NO-releasing compound, a hydrophobic base, an amphiphilic compound, optionally a solvent and/or cosolvent, optionally a thickening agent, and optionally one or more additives (e.g., a plasticizer, emollient, antioxidant, colorant, pigment, etc.). Example pastes and/or ointments include, but are not limited to, those described in International Application Publication No. WO 2013/138075, the contents of which are incorporated herein by referenced in its entirety.

In some embodiments, a nail coating composition (e.g., a nail paste and/or ointment) may comprise a NO-releasing compound in an amount of about 0.1% to about 70% by weight of the nail coating composition, a hydrophobic base (e.g., a hydrocarbon base and/or a hydrophobic polymer) in an amount of about 35% to about 90% by weight of the nail coating composition, an amphiphilic compound in an amount of about 1% to about 30% by weight of the nail coating composition, optionally a solvent and/or cosolvent in an amount of about 1% to about 30% by weight of the nail coating composition, optionally a thickening agent in an amount of about 1% to about 25% by weight of the nail coating composition, optionally one or more additives each optionally present in an amount of about 0.01% to about 20% by weight of the nail coating composition. In some embodiments, a nail coating composition may comprise two or more (e.g., 2, 3, 4, or more) hydrophobic bases and/or solvents. In some embodiments, the thickening agent may have a low water solubility, such as, for example a water solubility of about $5 \times 10^{-2}$ mg/L at 25° C. or less.

In some embodiments, a nail coating composition may be in the form of a nail lacquer. In some embodiments, a nail coating composition may be in the form of a nail paste, cream, and/or ointment. In some embodiments, a nail coating composition may be in the form of liquid or in the form of a gel and/or film.

In some embodiments, a nail coating composition may be applied to a nail of a subject and/or to skin surrounding the nail. The nail coating composition may provide and/or form a nail coating of the present invention on the nail and/or skin surrounding the nail. In some embodiments, a nail coating composition of the present invention may dry and/or cure to form a nail coating of the present invention. In some embodiments, a nail coating composition (e.g., a nail lacquer) may include one or more organic solvent(s) that may evaporate, optionally as the nail coating composition dries and/or cures, after topical application to a nail of a subject and/or to skin surrounding the nail to form a nail coating. A nail coating of the present invention may be in the form of a film. In some embodiments, the nail coating may be a semi-solid or hardened film.

A nail coating of the present invention may adhere to a nail of a subject and/or to skin surrounding the nail. In some embodiments, a nail coating described herein may adhere to keratin in a nail of a subject. In some embodiments, the nail coating may adhere to a nail (e.g., a natural and/or coated nail) for at least 1, 2, 3, 4, 5, 6, 7, 8, 9, 10 day(s), or more and may optionally adhere to the nail for at least 1, 2, 3, 4, 5, 6, 7, 8, 9, 10 day(s), or more without adhesion loss and/or breakdown of the coating (e.g., chipping, cracking, peeling, etc.).

A NO-releasing nail coating composition and/or nail coating described herein may be formed by any suitable method. In some embodiments, a NO-releasing nail coating composition may be formed by mixing the individual components of the composition and carrying out, when necessary, further processing appropriate for the particular formulation.

In some embodiments of the invention, a nail coating composition and/or nail coating is prepared by dissolving and/or dispersing a polymer (e.g., a film-forming and/or hydrophilic polymer) and/or a hydrophobic base, along with any other additives, into a solvent (e.g., an organic solvent); homogenizing the mixture; and then adding a NO-releasing compound (e.g., NO-releasing macromolecules) to the mixture to disperse the NO-releasing compound into the mixture. The NO-releasing compound may be added to the mixture under continuous agitation.

Any suitable packaging of a nail coating composition according to embodiments of the invention may be used. In some embodiments, a NO-releasing nail coating composition may be provided in sealed single dose container (e.g., a vial, such as a 10 mL vial) that is oxygen and moisture impermeable to prevent moisture from reaching the topical therapeutic and causing release of the nitric oxide. The container may be opened at the time of application and the product (i.e., the nail coating composition) may be applied to the surface of a nail of a subject and/or skin surrounding the nail. The product may be refrigerated until use to reduce the likelihood of premature release of the nitric oxide.

The NO-releasing nail coating compositions described herein may be a one-component formulation, such that it is not necessary to combine two or more compositions immediately prior to application. The nail coating composition may be applied as packaged, or in some cases, after agitation of the composition. In some embodiments, the one component NO-releasing nail coating composition may be in the form of a NO-releasing nail lacquer, paste, cream, gel, film, and/or ointment. Upon topical application to a nail of a subject and/or to skin surrounding the nail, the one-component formulation may release NO onto and/or into the nail and/or onto and/or into skin under and/or around the nail.

In some embodiments, a two component NO-releasing nail coating system is provided. One component of the two component NO-releasing nail coating system may include a nail coating composition as described herein (e.g., a NO-releasing nail lacquer, gel, film, paste, cream, and/or ointment) and the other component of the two component NO-releasing nail coating system may include a composition comprising a proton source (e.g., water). The composition comprising a proton source may initiate and/or increase the release NO from the nail coating composition and/or coating. In some embodiments, the composition comprising the proton source may increase the release of NO from the nail coating composition and/or coating by at least about 5%, 10%, 15%, 20%, 25%, 30%, 35%, 40%, 45%, 50%, 55%, 60%, 65%, 70%, 75%, 80%, 85%, 90%, 95%, 100%, 125%, 150%, 175%, 200%, or more compared to the release of NO from the nail coating composition and/or coating in the absence of the composition comprising the proton source.

The composition comprising the proton source may be topically applied to a nail of a subject and/or to the skin surrounding the nail at the same time that the nail coating composition is applied and/or at a given time before and/or after the nail coating composition is applied. For example, the composition comprising the proton source may be applied at about 1, 2, 3, 4, 5, 6, 7, 8, 9, 10, 11, 12, 13, 14, 15, 16, 17, 18, 19, 20, 21, 22, 23, 24 hour(s) or about 1, 2, 3, 4, 5, 6, 7, or more day(s) before and/or after the nail coating composition is applied to a nail of a subject and/or to the skin surrounding the nail. In some embodiments, the composition comprising the proton source is applied after the nail coating composition is applied.

A composition comprising a proton source may be applied onto a nail containing a nail coating composition and/or nail coating of the present invention. In some embodiments, the composition comprising a proton source is applied on top of or over the nail coating composition and/or nail coating of the present invention. In some embodiments, a composition comprising a proton source may be applied immediately after a nail coating composition of the present invention has been applied to a nail and/or after it has solidified and/or dried to form a nail coating of the present invention. In some embodiments, a composition comprising a proton source may be applied onto a nail containing a nail coating composition and/or nail coating 2 or more times, such as, for example, 2, 3, 4, or more times during a day; every day; every other day; every 3, 4, 5, or 6 days; once a week; etc.

The composition comprising the proton source may modify the release of NO from the nail coating composition and/or coating. In some embodiments, a composition, system, and/or method of the present invention may provide a continuous release or pulsatile release of NO from the NO nail coating composition and/or coating.

In some embodiments, the composition comprising the proton source may be provided in and/or on a substrate (e.g., a bandage, patch, dressing, tape, etc.). The substrate may be applied onto a nail of subject such that the composition comprising the proton source may contact the nail coating composition and/or coating and/or provide a proton to the nail coating composition and/or coating. In some embodiments, the substrate comprises a gaseous and/or moisture impermeable backing layer.

In some embodiments, the composition comprising a proton source may be in the form of a hydrogel. A hydrogel for use with a nail coating composition and/or nail coating of the present invention may comprise a gelling agent and water. Water may be present in a hydrogel in an amount of about 70% to about 99% by weight of the hydrogel. A gelling agent may be present in a hydrogel an amount of about 0.01% to about 10% by weight of the hydrogel, such as, for example, about 0.01% to about 5% by weight of the hydrogel. In some embodiments, the hydrogel may have a pH of about 3 to about 7, such as, for example, about 3.5 to about 6.5, about 3.5 to about 6, about 4 to about 5, or about 4 to about 4.5.

Example gelling agents include, but are not limited to, carboxypolymethylene; a polyacrylic polymer such as polyacrylic acid, a polyacrylate polymer, a cross-linked polyacrylate polymer, a cross-linked polyacrylic acid, and mixtures thereof; a cellulose ether such as hydroxyalkyl cellulose polymers such as hydroxypropyl methyl cellulose (HPMC), hydroxypropyl cellulose, hydroxyethyl cellulose, methyl cellulose, carboxymethyl cellulose, and salts and mixtures thereof; a methacrylate; a polyvinylpyrrolidone; cross-linked polyvinyl pyrrolidone; polyvinylpyrrolidone-vinyl acetate copolymer; polyvinylalcohol; polyethylene oxide; polyethylene glycol; polyvinylalkyl ether-maleic acid copolymer; a poloxamer; a carboxy vinyl polymer; a polysaccharide; a gum such as sodium alginate, carrageenan, xantham gum, gum acacia, arabic gum, guar gum, pullulan, agar, chitin, chitosan, pectin, karaya gum, zein, hordein, gliadin, locust bean gum, tragacantha, and mixtures thereof; a protein such as collagen, whey protein isolate, casein, milk protein, soy protein, gelatin, and mixtures thereof; a starch such as maltodextrin, amylose, high amylose starch, corn starch, potato starch, rice starch, tapioca starch, pea starch, sweet potato starch, barley starch, wheat starch, waxy corn starch, modified starch (e.g. hydroxypropylated high amylose starch), dextrin, levan, elsinan, gluten, and mixtures thereof; bentonite; calcium stearate; ceratonia; colloidal silicon dioxide; dextrin; hypromellose; polycarbophil; kaolin; saponite; sorbitan esters; sucrose; sesame oil; tragacanth; potassium alginate; povidone; sodium starch glycolate; phospholipids; alginate; and any combination thereof. In some embodiments, a gelling agent may be a cellulose, such as, but not limited to, a carboxymethyl cellulose or a salt thereof. In some embodiments, a gelling agent may be a commercially available gelling agent, such as, but not limited to, those commercially available from Lubrizol Corporation of Wickliffe, Ohio under the trade name Carbopol® (e.g., Carbopol® 980 Homopolymer Type C polymer, Carbopol® 980 NF polymer, Carpobol® 980P polymer, etc.).

Example hydrogels include, but are not limited to, those described in International Application Publication No. WO 2014/134502 and International Application No. PCT/US15/39908, the portions of which that are relevant to hydrogels are incorporated herein by reference in their entirety.

In some embodiments, the hydrogel may be provided in the form of a film. In some embodiments, the hydrogel may be in a form that can be peeled off of a backing layer and applied to a nail of a subject and/or to a nail coating composition and/or nail coating of the present invention. In some embodiments, the hydrogel may be a commercially available hydrogel, such as, but not limited to, those commercially available from Covidien or Axelgaard Manufacturing Co., Ltd.

Provided according to some embodiments is a kit. The kit may comprise a first composition comprising at least one NO-releasing compound and a second composition comprising a proton source (e.g., water). In some embodiments, the first composition may be a nail coating composition as described herein and the second composition may be a hydrogel as described herein. In some embodiments, the second composition may be provided on and/or in a substrate and/or in the form of a bandage, dressing, patch, or tape. In some embodiments, the first composition and the second composition may be separately stored.

In some embodiments, a packaged NO-releasing nail coating composition may be provided with a shelf life of at least about one week. In some embodiments, a packaged NO-releasing nail coating composition may have a shelf life of at least about four weeks, at least about 12 weeks, at least about 26 weeks, or at least about 52 weeks. In still further embodiments, a packaged NO-releasing nail coating composition may have a shelf life of from at least about 12 to at least about 104 weeks, or any range and/or individual value therein. As used herein, the term "shelf life" refers to the length of time that the product (i.e., a NO-releasing nail coating composition described herein) maintains the ability to release a therapeutically effective amount (e.g., a treatment and/or prevention effective amount) of nitric oxide in an unopened package stored under recommended storage conditions. The shelf life may, for example, be evidenced by the "use by" of "best if used by" date for the product, the manufacturer's expiration date of the product and/or the actual product characteristics after the specified period of time. Accordingly, the term "shelf life" as used herein should be construed as including both an "actual" shelf life of the product and a "predicted" shelf life of the product unless stated otherwise. As one skilled in the art will recognize, the rate of release of nitric oxide in a NO-releasing nail coating composition described herein under packaged and/or stored conditions may be different (i.e., faster or slower) than the rate of release of nitric oxide when the nail coating composition and/or nail coating is in use. In certain embodiments, the rate of release of nitric oxide may be faster when a nail coating composition and/or nail coating is in use compared to the rate of release of nitric oxide when the nail coating composition was packaged and/or stored.

In some embodiments, the shelf life of the product is the time that the product maintains the ability to release at least 50% of the initial amount nitric oxide that the product may release when packaged. In further embodiments, the shelf life of the product is the time that the product maintains the ability to release at least 70%, at least 80%, at least 90%, at least 95%, or at least 98% of the initial amount nitric oxide that the product may release when packaged. In some embodiments, the recommended storage conditions are room temperature. In some embodiments, the recommended storage conditions are refrigerated storage conditions. In particular embodiments, the refrigerated storage conditions are in a range from about 1° C. to about 12° C.

Further embodiments may provide packaged NO-releasing nail coating compositions that have a useful life of at least about 7 days after opening the package. In further embodiments, the useful life is at least about 30 days, at least about 60 days or at least about 90 days. In still further embodiments, a packaged NO-releasing nail coating composition may have a useful life of from at least about 60 days to at least about 730 days, or any range and/or individual value therein. As used herein, the term "useful life" refers to the length of time that the product maintains the ability to release a therapeutically effective amount of nitric oxide from an opened packaged when applied as recommended and when stored under recommended storage conditions. The useful life may, for example, be evidenced by the manufacturer's recommended time to dispose of the product after opening or measurements of the products characteristics after opening. Accordingly, the term "useful life" as used herein should be construed as including both an "actual" useful life of the product and a "predicted" useful life of the product unless stated otherwise. In some embodiments, the useful life of the product is the time that the product maintains the ability to release at least 50% of the initial amount nitric oxide that the product may release when the package is opened. In further embodiments, the shelf life of the product is the time that the product maintains the ability to release at least 70%, at least 80%, at least 90%, at least 95%, or at least 98% of the initial amount nitric oxide that the product may release when the package is opened. In some embodiments, the recommended storage conditions after opening are room temperature. In particular embodiments, the recommended storage conditions after opening are refrigerated conditions.

According to some embodiments of the invention, provided are methods of treating a subject by contacting a subject with a nail coating composition and/or nail coating according to embodiments of the invention. Thus, by contacting the subject with the NO-releasing nail coating composition and/or nail coating, the subject may be treated with nitric oxide.

In some embodiments, a method of treating and/or preventing a nail disease and/or disorder in a subject may comprise topically applying a nail coating composition described herein to a nail of the subject, thereby treating and/or preventing the nail disease or disorder. In some embodiments, a method of the present invention may comprise topically applying a NO-releasing nail coating composition described herein to a nail to form a NO-releasing coating. The NO-releasing coating composition and/or coating may adhere to and/or cover the area of the nail to which it is applied. In some embodiments, the method may comprise topically applying to the nail a two-component NO-releasing nail coating system as described herein.

"Nail" as used herein may refer to any part of a fingernail and/or a toenail of a subject. A nail may be a full or partially intact nail. A nail may be a healthy nail, a diseased nail, and/or a damaged nail. A method disclosed herein may treat and/or prevent a nail disease and/or disorder in a nail of a subject. A NO-releasing coating composition described herein may be applied to all or any portion of a subject's nail. In some embodiments, a method may comprise applying a NO-releasing coating composition described herein to a nail and/or to the skin surrounding the nail such as, but not limited to, the cuticle.

The terms "treat", "treating", and grammatical variants thereof, as used herein in reference to treating a subject, refer to any type of treatment that imparts a benefit to a subject and may mean that the severity of the subject's condition is reduced, at least partially improved or ameliorated and/or that some alleviation, mitigation or decrease in at least one clinical symptom associated with the condition is achieved and/or there is a delay in the progression of the nail disease or disorder. In some embodiments, the severity of a subject's condition may be reduced compared to the severity of the condition in the absence of a method of the present invention. A method of the present invention may provide the total absence of the disease, disorder, infection, wound, and/or clinical symptom in the subject. A method of the present invention may also provide partial treatment, such as relieving and/or reducing the effects and/or severity of the disease, disorder, infection, wound, and/or clinical symptom in the subject and/or delaying the progression and/or onset of the disease, disorder, infection, wound, and/or clinical symptom compared to what would occur in the absence of the methods of the present invention.

The terms "prevent," "preventing", "prevention", and grammatical variations thereof refer to avoidance, reduction and/or delay of the onset of a nail disease, disorder and/or a clinical symptom(s) in a subject and/or a reduction in the severity of the onset of the nail disease, disorder and/or clinical symptom(s) relative to what would occur in the absence of a method of the present invention. The prevention may be complete, e.g., the total absence of the nail disease, disorder and/or clinical symptom(s). The prevention may be partial, such that the occurrence of the nail disease, disorder and/or clinical symptom(s) in the subject and/or the severity of onset is less than what would occur in the absence of a method of the present invention.

The term "contacting" and grammatical variants thereof, refers to coating, submerging, painting, exposing, immersing, dipping, wetting, pasting, sticking, dousing, washing, rinsing, soaking, plunging, dunking, dampening, and/or placing any portion of the subject (e.g., a nail) into contact with a nail coating composition, nail coating, and/or composition comprising a proton source (e.g., a hydrogel) for any duration of time. In certain embodiments of the present invention, the subject is exposed to and/or in contact with a NO-releasing nail coating composition and/or nail coating for a time sufficient to obtain a treatment effective and/or a prevention effective amount of nitric Oxide.

A "treatment effective" amount as used herein is an amount that is sufficient to treat (as defined herein) the subject. Those skilled in the art will appreciate that the therapeutic effects need not be complete or curative, as long as some benefit is provided to the subject.

A "prevention effective" amount as used herein is an amount that is sufficient to prevent (as defined herein) a nail disease, disorder and/or clinical symptom in a subject. Those skilled in the art will appreciate that the level of prevention need not be complete, as long as some benefit is provided to the subject.

The present invention finds use in both veterinary and medical applications, including drug screening and drug development purposes. Suitable subjects of the present invention include, but are not limited to avians and mammals. The term "avian" as used herein includes, but is not limited to, chickens, ducks, geese, quail, turkeys, pheasants, ratites (e.g., ostrich), parrots, parakeets, macaws, cockatiels, canaries, finches, and birds in ovo. The term "mammal" as used herein includes, but is not limited to, primates (e.g., simians and humans), non-human primates (e.g., monkeys, baboons, chimpanzees, gorillas), bovines, ovines, caprines, ungulates, porcines, equines, felines, canines, lagomorphs, pinnipeds, rodents (e.g., rats, hamsters, and mice), and mammals in utero. In some embodiments of the present invention, the subject is a mammal and in certain embodiments the subject is a human. Human subjects include both males and females and subjects of all ages including fetal, neonatal, infant, juvenile, adolescent, adult, and geriatric subjects. Subjects may be treated for any purpose, such as, but not limited to, treatment and/or prevention of infection.

In particular embodiments of the present invention, a nail coating composition and/or nail coating may be used to treat onychomycosis or any other infection of the nail and/or skin beneath and/or around the nail caused by a fungus, bacteria, virus, yeast, and/or mold. In some embodiments, a nail coating composition and/or nail coating according to embodiments of the invention may be used to treat other ailments and/or conditions of the nail and/or skin surrounding and/or beneath the nail, either via anti-microbial action, anti-inflammatory action, and/or by any other mechanism. Example nail ailments and/or conditions include, but are not limited to, nail psoriasis, paronychia infection, nail dystrophy, nail brittleness, nail pitting, nail peeling, nail clubbing, nail separation, dermatophytosis, psoriatic nail dystrophy, onychia, onychiagryposis, onychia trophia, onychocryptosis, onychodystrophy, onychomycosis, onychogryposis, onycholysis, onychomadesis, onychauxis, onychorrhexis, onychoschizia, tinea unguium, onychophosis, onychoptosis, paronychia, pseudomonas, pterygium and pterygium inversum unguis, koilonychia, subungual hematoma or other trauma to the nail, folic acid deficiency, subungual hyperkeratosis, leukonychia, nail patella syndrome, melanonychia, protein deficiency, methyl methacrylate damaged nails, vitamin C deficiency, vitamin deficiency, tinea unguis, thinning nails associated with lichen planus, Raynaud's disease, nail dystrophy associated with rheumatoid arthritis, beau's lines, Mee's lines associated with certain kinds of poisoning, discoloration, lamellar splitting, longitudinal grooves and/or ridges, transverse grooves, pitting, soft nails, brittle nail syndrome, and any combination thereof.

In some embodiments, a method of improving the appearance of a nail may be provided. The method may comprise topically applying a nail coating composition (e.g., a one component coating composition) and/or nail coating described herein to the nail of a subject, thereby improving the appearance of the nail. In some embodiments, the method may comprise applying a two component NO-releasing nail coating system as described herein. In some embodiments, the appearance of the nail may be improved compared to the appearance of a nail in the absence of a method of the present invention.

In some embodiments, a method of the present invention may improve the appearance of a nail by increasing or improving nail health compared to nail health in the absence of a method of the present invention. Nail health may be evaluated by how the nail grows, the nail color, the smoothness of the nail, the shape of the nail, and/or the thickness of the nail. For example, the method may increase and/or improve nail health by decreasing yellowing and/or discoloration of a nail (e.g., due to onychomycosis); decreasing nail dullness; decreasing nail ridges (e.g., longitudinal and/or horizontal ridges), pits, and/or the like; decreasing nail peeling, splitting, cracking, and/or the like; increasing proper nail growth; decreasing nail thickness; decreasing onycholysis; decreasing subungual hyperkeratosis; increasing nail strength; and any combination thereof.

Improvement in the appearance of a nail may be determined by a visual assessment of the nail, such as by visually assessing the color, surface smoothness, shape, and/or thickness. In some embodiments, a method of the present invention may improve nail strength compared to the strength of a nail in the absence of a method of the present invention.

Such methods may be used in combination with any other known methods of treatment, including the application of other therapeutic agents, such as those that have anti-inflammatory, pain-relieving, immunosuppressant, vasodilating, wound healing and/or anti-biofilm-forming properties. For the methods used herein, additional therapeutic agents and methods may be used prior to, concurrently with and/or after contact with a nail coating composition and/or nail coating of the present invention.

The invention will now be described further with respect to the foregoing examples. It should be appreciated that these examples are for the purpose of illustrating the invention, and do not limit the scope of the invention as defined by the claims

EXAMPLES

Example 1: Vehicle Nail Lacquer

Vehicle nail lacquer solutions were initially prepared to evaluate the film-forming potential, upon solvent evaporation, of formulations comprised of a single polymer. Additional nail lacquer vehicles were prepared to evaluate formulations containing combinations of a strong film-forming polymer and a hydrophilic polymer. While not wishing to be bound to any particular theory, the intention of the binary polymer formulations is that the hydrophilic polymer will form channels within a robust, protective film allowing moisture penetration without disrupting or dissolving the film.

The vehicle nail lacquers were prepared by first mixing weighed amounts of the solvents and emollient in a 250-mL glass beaker. The weighed amount of polymer was then dissolved in the mixture using an IKA T-18 Homogenizer at a low-to-medium speed setting. The resulting solution was transferred to a 20-mL glass vial, and the visual appearance of the solution was recorded as provided in Table 2. The prototype vehicle formulations that were evaluated are summarized in Table 1.

TABLE 1

| | Vehicle Nail Lacquer Formulations | | | | | | | | | |
|---|---|---|---|---|---|---|---|---|---|---|
| Ingredient | VNL-01 % w/w | VNL-02 % w/w | VNL-03 % w/w | VNL-04 % w/w | VNL-05 % w/w | VNL-06 % w/w | VNL-07 % w/w | VNL-08 % w/w | VNL-09 % w/w | VNL-10 % w/w |
| Denatured alcohol, anhy. | 78.0 | 75.0 | 70.0 | 70.0 | 70.0 | 70.0 | 70.0 | 72.0 | 72.0 | 72.0 |
| Acetone, anhy. | 15.0 | 15.0 | 15.0 | 15.0 | 15.0 | 15.0 | 15.0 | 15.0 | 15.0 | 15.0 |

TABLE 1-continued

Vehicle Nail Lacquer Formulations

| Ingredient | VNL-01 % w/w | VNL-02 % w/w | VNL-03 % w/w | VNL-04 % w/w | VNL-05 % w/w | VNL-06 % w/w | VNL-07 % w/w | VNL-08 % w/w | VNL-09 % w/w | VNL-10 % w/w |
|---|---|---|---|---|---|---|---|---|---|---|
| Isopropyl palmitate | 5.0 | 5.0 | 5.0 | 5.0 | 5.0 | 5.0 | 5.0 | 5.0 | 5.0 | 5.0 |
| ETHOCEL STD-10P | 2.0 | 5.0 | 10.0 | — | — | — | — | 5.0 | 5.0 | — |
| EUDRAGIT E 100 | — | — | — | — | — | — | 10.0 | — | — | — |
| EUDRAGIT RL 100 | — | — | — | — | — | 10.0 | — | — | — | 5.0 |
| KOLLIDON VA64 | — | — | — | — | 10.0 | — | — | 3.0 | — | — |
| PVP | — | — | — | 10.0 | — | — | — | — | 3.0 | 3.0 |
| % Total | 100.0 | 100.0 | 100.0 | 100.0 | 100.0 | 100.0 | 100.0 | 100.0 | 100.0 | 100.0 |

Each lacquer vehicle was evenly spread across glass microscope slides using a small paintbrush to measure the solvent evaporation time and apparent film quality upon solvent evaporation. The resulting polymer film was also assigned a "Film Grade" ranging from 1 to 5, with 5 being the highest grade. The results of the formulation assessments are summarized in Table 2.

Example 2: Nitric-Oxide Releasing Nail Lacquer

A diazeniumdiolate-functionalized co-condensed silica (Nitricil™) was prepared according to known methods and milled. Nitricil™ is a NO-releasing co-condensed silica, from Novan, Inc. and may be provided with one or more different release profiles and/or functional groups, such as, but not limited to, diazeniumdiolate-functionalized co-con-

TABLE 2

Vehicle Nail Lacquer Results Summary

| Formulation Reference | Polymer (% w/w) | Solution Appearance | Evaporation Time (sec.) | Apparent Film Quality | Film Grad |
|---|---|---|---|---|---|
| VNL-01 | 2% ETHOCEL STD-10P | Clear, faint-to-light yellow solution | 32 | Colorless, continuous film. Film appears to be fragile but have good adhesion. | 3 |
| VNL-02 | 5% ETHOCEL STD-10P | Clear, light yellow solution | 28 | Colorless, continuous film. Film appears to be robust and have good adhesion. | 5 |
| VNL-03 | 10% ETHOCEL STD-10P | Clear, light yellow solution | 29 | Colorless, continuous film. Film appears to be rigid and have good adhesion. | 4 |
| VNL-04 | 10% PVP (MW 40,000) | Clear, colorless solution | 58 | Hazy, continuous film. Film appears to be fragile and have poor adhesion. | 2 |
| VNL-05 | 10% KOLLODON VA64 | Clear, colorless solution | 62 | Slightly hazy, continuous film. Film appears to be robust but have poor adhesion. | 3 |
| VNL-06 | 10% EUDRAGIT RL 100 | Clear, light yellow solution | 51 | Colorless, continuous film. Film appears to be robust and have good adhesion. | 4 |
| VNL-07 | 10% EUDRAGIT E 100 | Clear, light yellow solution | 49 | Colorless, continuous film. Film appears to be robust and have good adhesion. | 4 |
| VNL-08 | 5% ETHOCEL STD-10P 3% KOLLIDON VA64 | Clear, light yellow solution | 68 | Colorless, continuous film. Film appears to be robust and have good adhesion. | 5 |
| VNL-09 | 5% ETHOCEL STD-10P 3% PVP | Clear, light yellow solution | 57 | Slightly hazy, continuous film. Film appears to be robust and have good adhesion. | 4 |
| VNL-10 | 5% EUDRAGIT RL 100 3% KOLLIDON VA64 | Clear, light yellow solution | 74 | Colorless, continuous film. Film appears to be robust and have good adhesion. | 4 | densed silica. Nitricil™ was analyzed for nitric oxide (NO) content, moisture content, and the particle size distribution of pre-milled and milled Nitricil™ was determined prior to initiation of the formulation development. The results from the analyses are summarized in Table 3.

TABLE 3

Diazeniumdiolate-functionalized Co-Condensed Silica Properties

|  | NO Content | Moisture Content | Particle Size Distribution - Pre-Milled | Particle Size Distribution - Milled |
|---|---|---|---|---|
| Result | 4.57 µmol/mg (13.71% w/w) | 6.1% w/w | $D_{10}$: 18.90 µm $D_{50}$: 442.38 µm $D_{90}$: 843.41 µm | $D_{10}$: 1.25 µm $D_{50}$: 4.34 µm $D_{90}$: 10.59 µm |

The initial development of the Nitricil™ Nail Lacquer was based on vehicle formulation reference VNL-8 to contain 2% Nitricil™ and to deliver 0.3% NO. The lacquer was prepared in a 250-mL glass beaker by dissolving the polymers in the solvent and emollient mixture using an IKA T-18 Homogenizer at a low-to-medium speed setting. While under continuous agitation, the weighed amount of Nitricil™ was added and dispersed into the mixture. The resulting lacquer suspension was transferred to 5 separate 20-mL glass vials, and the visual appearance of the suspension was recorded as provided in Table 5. The formulation prepared is summarized in Table 4.

TABLE 4

NVN1000 Nail Lacquer, 2% (0.3% NO)

| Ingredient | ANL-01 % w/w |
|---|---|
| Denatured alcohol, anhydrous | 70.0 |
| Acetone, anhydrous | 15.0 |
| Isopropyl palmitate | 5.0 |
| ETHOCEL STD-10P | 5.0 |
| KOLLIDON VA64 | 3.0 |
| Nitricil ™ | 2.0 |
| % Total | 100.0 |

A sample of the Nitricil™ Nail Lacquer was submitted to test the NO content and moisture content of the formulation. The lacquer was also spread evenly across glass microscope slides using a small paintbrush to measure the solvent evaporation time and apparent film quality upon solvent evaporation. The resulting film was also assigned a "Film Grade" ranging from 1 to 5, with 5 being the highest grade. The results of the formulation assessments are summarized in Table 5.

TABLE 5

Nitricil ™ Nail Lacquer Results Summary

| Formulation Reference | NO Content | Moisture Content | Solution Appearance | Evaporation Time | Apparent Film Quality | Film Grade |
|---|---|---|---|---|---|---|
| ANL-01 | 0.3% w/w | 0.7% w/w | Opaque, faintly yellow suspension | 64 sec | Hazy, continuous film. Film appears to be robust with good adhesion. | 5 |

Example 3: Additional Vehicle Nail Lacquers

Additional example vehicle nail lacquers are provided in Formulas 1-5 below. A NO-releasing compound (e.g., a diazeniumdiolate-functionalized co-condensed silica) may be added to an example vehicle nail lacquer in an amount of about 0.1% to about 70% by weight of the lacquer composition.

Formula 1

| Ingredient | %/Weight | Function |
|---|---|---|
| Isopropyl Alcohol | 65-85 | Solvent |
| Nitrocellulose | 1-12 | Film Former |
| Adipic Acid/Neopentyl Glycol/Trimellitic Anhydride Copolymer | 1-12 | Film Former |
| Trimethyl Pentanyl Diisobutyrate | 1-6 | Plasticizer |
| Triphenyl Phosphate | 1-6 | Plasticizer |
| Stearalkonium Hectorite | 1-2 | Thickening Agent |
| Benzophenone-1 | 0.1 | Antioxidant |
| Titanium Dioxide | Quantity sufficient | Colorant |

Formula 2

| Ingredient | %/Weight | Function |
|---|---|---|
| PNVA | 1-3 | Film Former |
| Isopropyl Alcohol | 30-80 | Solvent |
| Propylene Glycol | 1-10 | Solvent |
| Glycerine | 1-10 | Solvent |

Formula 3

| Ingredient | %/Weight | Function |
|---|---|---|
| Gantrez S-97 | 1-10 | Film Former |
| Isopropyl Alcohol | 30-80 | Solvent |
| Propylene Glycol | 1-10 | Solvent |
| Glycerin | 1-10 | Solvent |

Formula 4

| Ingredient | %/Weight | Function |
|---|---|---|
| Plasdone S-630 | 1-20 | Film Former |
| Isopropyl Alcohol | 30-80 | Solvent |
| Propylene Glycol | 1-10 | Solvent |
| Glycerin | 1-10 | Solvent |

Formula 5

| Ingredient | %/Weight | Function |
|---|---|---|
| Plasdone S-630 | 1-20 | Film Former |
| Isopropyl Alcohol | 30-80 | Solvent |
| Propylene Glycol | 1-10 | Solvent |
| Glycerin | 1-10 | Solvent |

Example 4: Nail Paste or Ointment Formulations

Ranges for ingredients in example nail paste or ointment formulations are provided in Formula 6 below.

Formula 6

| Ingredient | %/Weight | Function |
|---|---|---|
| Nitricil ™ | 0.01-50 | Active Pharmaceutical Ingredient (API) |
| Crodabase SQ | 0-40 | Hydrocarbon Base |
| Petrolatum, White, USP | 0-40 | Hydrocarbon Base |
| Miglyol 812 | 0-10 | Solvent |
| Cetyl Alcohol, NF | 1-7 | Thickening Agent |
| Mineral Oil, USP | 1-6 | Solvent |
| Softigen 767 | 1-2 | Amphiphilic agent/Solvent |

The foregoing is illustrative of the present invention, and is not to be construed as limiting thereof. The invention is defined by the following claims, with equivalents of the claims to be included therein. All publications, patent applications, patents, patent publications, and other references cited herein are incorporated by reference in their entireties for the teachings relevant to the sentence and/or paragraph in which the reference is presented.

That which is claimed is:

1. A nitric oxide (NO)-releasing nail coating composition comprising NO-releasing co-condensed silica at a concentration in a range of about 0.1% to about 70% by weight percent of the composition;
at least one hydrophilic polymer at a concentration in a range of about 1% to about 15% by weight percent of the composition;
at least one film-forming polymer at a concentration in a range of about 1% to about 25% by weight percent of the composition, the at least one film-forming polymer selected from the group consisting of nitrocellulose, methyl vinyl ether/maleic acid copolymer, vinyl pyrrolidone/vinyl acetate copolymer, poly N-vinylacetamide/sodium acrylate copolymer, ethyl cellulose, methacrylate polymer, methacrylate copolymer, and cellulose acetate; and
an organic solvent at a concentration in a range of about 30% to about 98% by weight percent of the composition,
wherein the composition forms a lacquer when dried or cured, wherein the lacquer allows moisture penetration sufficient to release at least a portion of the NO from the NO-releasing co-condensed silica, and
wherein the NO-releasing co-condensed silica is in the form of particles that are suspended in the composition.

2. The NO-releasing nail coating composition of claim 1, wherein the NO-releasing co-condensed silica comprises diazeniumdiolate functional groups.

3. The NO-releasing nail coating composition of claim 1, wherein the at least one film-forming polymer comprises at least one of nitrocellulose, ethyl cellulose and cellulose acetate.

4. The NO-releasing nail coating composition of claim 1, wherein the at least one organic solvent comprises at least one solvent selected from the group consisting of acetone, ethyl acetate, ethyl alcohol, denatured alcohol, isopropyl alcohol, and any combination thereof.

5. The NO-releasing nail coating composition of claim 1, wherein the at least one hydrophilic polymer comprises polyvinylpyrolidone polymer (PVP) and/or copolymers thereof.

6. The NO-releasing nail coating composition of claim 1, further comprising one or more additive(s), optionally wherein each of the one or more additive(s) is present in an amount of about 0.01% to about 20% by weight of the composition.

7. The NO-releasing nail coating composition of claim 1, wherein the at least one hydrophilic polymer is present in the composition at a concentration in a range from about 1% to about 10% by weight percent of the composition; the at least one film-forming polymer is present in the composition at a concentration in a range from about 1% to about 10% by weight percent of the composition; and the organic solvent is present in the composition at a concentration in a range from about 75% to about 98% by weight percent of the composition.

8. The NO-releasing nail coating composition of claim 1, wherein the NO storage of the composition is in a range from about 1 nmol NO/mg to about 2.5 μmol NO/mg.

9. The NO-releasing nail coating composition of claim 1, wherein the NO-releasing nail coating composition has a shelf life in a range from about 12 to about 104 weeks.

10. The NO-releasing nail coating composition of claim 1, wherein the NO-releasing nail coating composition has a useful life in a range from about 60 to about 730 days.

11. The NO-releasing nail coating composition of claim 1, wherein the NO-releasing co-condensed silica is diazeniumdiolate-functionalized co-condensed silica and the diazeniumdiolate-functionalized co-condensed silica is present in the composition at a concentration in a range of about 0.1% to about 25% by weight of the composition;
wherein the at least one hydrophilic polymer is PVP and/or a copolymer thereof and the PVP and/or copolymer thereof is present in the composition at a concentration in a range of about 1% to about 10% by weight of the composition;
wherein the at least one film-forming polymer is ethyl cellulose and the ethyl cellulose is present in the composition at a concentration in a range of about 1% to about 10% by weight of the composition; and the organic solvent is present in the composition at a concentration in a range of about 75% to about 97.9% by weight of the composition.

12. The NO-releasing nail coating composition of claim 1, wherein, after application to a nail of a subject, NO is released in an amount of about 0.05% to about 20% by weight of the composition.

13. A two component NO-releasing nail coating system comprising:
a first composition comprising the NO-releasing nail coating composition of claim 1; and
a second composition comprising a proton source.

14. The two component NO-releasing nail coating system of claim 13, wherein the NO-releasing co-condensed silica is present in the composition at a concentration in a range of about 0.1% to about 50% by weight percent of the composition.

15. The two component NO-releasing nail coating system of claim 13, wherein the second composition is in the form of a hydrogel, optionally wherein the second composition is provided in and/or on a substrate.

16. A kit comprising:
a first composition comprising the NO-releasing nail coating composition of claim 1; and
a second composition comprising a proton source.

17. The kit of claim 16, wherein the first composition and the second composition are separately stored.

18. The NO-releasing nail coating composition of claim 1, wherein the at least one hydrophilic polymer is selected from the group consisting of hydroxypropyl methyl cellulose, hydroxypropyl cellulose, methylcellulose, polyvinylpyrrolidone polymers, polyvinylpyrrolidone copolymers, sodium carboxy methylcellulose, and polyvinyl alcohol.

19. A method of treating a fungal infection of a nail of a subject comprising:
contacting the nail with the NO-releasing nail coating composition of claim 1 for a time sufficient to treat the fungal infection.

20. A method of improving the appearance of a nail of a subject comprising:
topically applying the NO-releasing nail coating composition of claim 1 to said nail of said subject, thereby improving the appearance of said nail.

\* \* \* \* \*